United States Patent [19]

Johnson et al.

[11] 4,189,568

[45] Feb. 19, 1980

[54] ANTIBIOTIC PURIFICATION PROCESS

[75] Inventors: David L. Johnson; Terrence W. Doyle, both of Fayetteville, N.Y.

[73] Assignee: Bristol-Myers Company, New York, N.Y.

[21] Appl. No.: 875,972

[22] Filed: Feb. 8, 1978

[51] Int. Cl.² ............................................. C07H 15/24
[52] U.S. Cl. .................................................. 536/17 A
[58] Field of Search ........................................... 536/17

[56] References Cited
FOREIGN PATENT DOCUMENTS 1426637  3/1976  United Kingdom ...................... 424/181

OTHER PUBLICATIONS

Brazhnikova et al., J. Antibiotics, 27, pp. 254–259, (1974).

*Primary Examiner*—Jerome D. Goldberg
*Attorney, Agent, or Firm*—David M. Morse

[57] ABSTRACT

Carminomycin 1, a known antibiotic, is obtained in a highly purified form from crude fermentation solids containing it by use of a novel multistep purification process involving solvent extraction, countercurrent distribution and adsorption chromatography.

2 Claims, No Drawings

ANTIBIOTIC PURIFICATION PROCESS

BACKGROUND OF THE INVENTION (1) Field of the Invention

This invention relates to a novel multistep process for purifying carminomycin 1, a known anthracycline antibiotic.

(2) Description of the Prior Art

Carminomycin 1 is a known antitumor antibiotic which has been isolated from the fermentation broth of *Actinomadura carminata* as described in U.K. Pat. No. 1,426,637 and in *J. Antibiotics,* 27, 254 (1974). According to the above references, carminomycin is recovered from the culture medium by extraction with an organic solvent such as chloroform or carbon tetrachloride followed by chromatography over silicic acid.

Isolation of carminomycin 1 from an antibiotic complex (figaroic acid complex) produced by fermentation of Streptosporangium sp. strain C-31,751 (ATCC 31129) has been described by our colleagues W. T. Bradner, D. E. Nettleton, Jr. and J. A. Bush in U.S. Application Ser. No. 832,034 filed Sept. 9, 1977; the entire disclosure of that application is incorporated herein by reference. In this process, the fermentation complex is extracted into an organic solvent (e.g. $CH_3OH$ or a mixture of $CH_3OH$ and $CHCl_3$), the organic extract is subjected to mild acid hydrolysis to preferentially form carminomycin 1 and the carminomycin 1 is recovered by evaporation and purified by chromatography over Sephadex LH-20.

A procedure for isolating carminomycin 1 from the fermentation broth of Streptosporangium sp. has been disclosed by M. E. Wall, et al. in *J. Amer. Chem. Soc.,* 97(20), 5955 (1975). In the Wall procedure, the fermentation broth is extracted with methyl isobutyl ketone, the extract is concentrated and the crude fermentation solids are precipitated by addition of Skellysolve B (isomeric hexanes). The crude fermentation solids are then chromatographed on silicic acid using a gradient eluant of 4:1 (v/v) chloroform: acetone containing 5% $CH_3OH$ with increasing gradients of $CH_3OH$ up to 50%.

In view of the increasing interest in carminomycin 1 for treatment of human cancers, there is a need for a new commercially feasible purification process which would allow this antibiotic to be prepared in a highly purified form suitable for pharmaceutical use.

Accordingly, it is an object of the present invention to provide a process for preparing highly purified carminomycin 1 from crude or impure carminomycin 1. It is a further object to provide such a purification process which would be economically practical in the production of commercial quantities of carminomycin 1. A still further object is to provide a purification process which is applicable to impure carminomycin 1 derived from either Streptosporangium sp. ATCC 31129 or *Actinomadura carminata*, or carminomycin 1-producing mutants thereof.

The foregoing objectives have been achieved by the provision according to the present invention of a process for providing the antibiotic carminomycin 1 in purified form from crude fermentation solids containing said antibiotic which comprises the consecutive steps of (1) slurrying crude fermentation solids containing carminomycin 1, preferably fermentation solids coated onto diatomaceous earth, with methylene chloride and filtering said slurry to recover the filter cake;

(2) washing the filter cake with water;

(3) extracting the filter cake from step (2) with methanol and recovering a solid from the concentrated filtered extract by concentration to dryness or precipitation with an antisolvent;

(4) dissolving the solid from step (3) in equal volumes of the upper and lower phases of the solvent system consisting of methylene chloride, ethanol, carbon tetrachloride and water (2:1:2:1 v/v); said dissolution being accomplished by first dissolving the solid in a 1:1 (v/v) mixture of methylene chloride and ethanol and then adding to this solution ethanol, carbon tetrachloride, solvent upper phase of the system $CCl_4:CH_2Cl_2:C_2H_5OH:H_2O$ (2:1:2:1) (v/v) and water in that order in an amount sufficient to provide a final solvent system as defined above;

(5) subjecting said solution of step (4) to a countercurrent distribution procedure, said procedure comprising the consecutive steps of:

(a) providing a countercurrent distribution apparatus having a plurality of packed solvent columns connected in series, said columns being packed with conventional glass or ceramic column packing material;

(b) filling all except the first column with the upper phase of the solvent system $CCl_4:CH_2Cl_2:C_2H_5OH:H_2O$ (2:1:2:1) (v/v);

(c) filling the first column with the upper phase of the solution from step (4);

(d) dispersing the lower phase of the solution from step (4) through the columns while collecting samples of the effluent from the last column until all of the solvent has been employed;

(e) dispersing the lower phase of the solvent system $CCl_4:CH_2Cl_2:C_2H_5OH:H_2O$ (2:1:2:1) (v/v) through the columns while collecting samples of the effluent from the last column until thin layer chromatographic analysis of the various samples and solutions in the columns indicates cessation of any significant separation of components;

(f) analyzing the samples taken and the solutions from the columns by thin layer chromatography to detect the carminomycin 1-rich solvent fractions;

(g) combining the carminomycin 1-rich solvent fractions and recovering the impure carminomycin 1 solids from said combined fractions;

(6) dissolving the solids from step (5) in chloroform:methanol (17:3) (v/v);

(7) adsorbing the solution from step (6) on silica gel which has been slurried with chloroform:methanol (17:3) (v/v) and adjusted to a pH of about 7–9; and (8) eluting the components of the impure carminomycin 1 mixture with a solvent system consisting of chloroform:methanol (17:3) (v/v) to produce purified carminomycin 1.

The present invention may advantageously be employed with any source of impure carminomycin 1 but is most useful for purification of crude fermentation solids derived from culture broths of carminomycin 1-producing strains of *Actinomadura carminata* or Streptosporangium sp. (i.e. Streptosporangium sp. ATCC 31129 or a carminomycin 1-producing mutant thereof). Such crude fermentation solids may be obtained from the fermentation medium by known methods, e.g. by extraction of the filtered broth or whole broth with a water-immiscible organic solvent such as methylene chloride or methyl isobutyl ketone and recovery of the carminomycin 1-containing fermentation solids from the organic extract by concentration to dryness or by concentration and precipitation with an appropriate antisolvent, e.g. diethyl ether, benzene or a liquid aliphatic hydrocarbon such as n-hexane, n-heptane or isomeric hexanes (Skellysolve B) in the case of the antibiotic complex (designated figaroic acid complex) from Streptosporangium sp. and ethyl acetate, benzene, chloroform, diethyl ether or petroleum ether in the case of the antibiotic complex from *Actinomadura carminata*. The purification procedure of the present invention is most efficient when the crude carminomycin 1 is recovered from the fermentation broth coated onto diatomaceous earth (filter aid) by a procedure such as illustrated in Preparation A-3 below.

The crude carminomycin 1-coating fermentation solids are commonly contaminated with filter aid (diatomaceous earth), fats, sugars, defoaming agents and other biologically inactive materials associated with the fermentation and preferred recovery steps. To separate such contaminants from the biologically active components, the fermentation solids are subjected to a solvent extraction and wash procedure as described in steps 1–3 above. Thus, the crude carminomycin 1 solids are first slurried with methylene chloride. The slurry is then filtered and the filter cake washed with methylene chloride. Advantageously this procedure is repeated one or more times. The filter cake from the methylene chloride wash is next washed with water one or more times to remove water-soluble impurities such as sugars. The washed filter cake is then extracted with methanol, the methanol extract filtered and concentrated and the carminomycin 1-containing solids recovered from the concentrated extract by precipitation with an appropriate antisolvent (e.g. diethyl ether, benzene or a liquid aliphatic hydrocarbon or mixture of hydrocarbons such as n-hexane, n-heptane or isomeric hexanes) or by evaporation to dryness.

Following steps (1) through (3), the impure carminomycin 1 solids recovered from the methanol extract are subjected to a countercurrent distribution procedure to separate the antibiotic mixture into component groups closely related into polarity. Separation by countercurrent distribution may be carried out with any conventional apparatus, e.g. a Craig apparatus. In the production of larger than laboratory quantities of purified carminomycin 1, however, it is preferred to employ a series of packed solvent columns such as are commonly used in large scale pilot plant or industrial extractions.

An apparatus found to be especially advantageous for the purposes of the present invention may be constructed by connecting in series a plurality (preferably at least 5) of packed solvent columns, e.g. Glenco solvent columns distributed by Glenco Scientific Inc., Houston, Texas. The columns are connected, e.g. with Teflon or polyethylene tubing, from the bottom of one column to the top of the next. While good results have been obtained with five solvent columns, acceptable separation can be achieved with any number of columns from two to several hundred. The columns are filled with conventional glass or ceramic packing material such as Raschig rings or Berl saddles.

The impure carminomycin 1 from step (3) of the process is dissolved in a two phase (equal volumes of each phase) solvent system consisting of methylene chloride, ethanol, carbon tetrachloride and water in the volume ratio of 2:1:2:1, respectively. The method of dissolution, however, is critical for obtaining significant amounts of the solid in solution in a practical time period. Thus, the solid is first dissolved in a 1:1 v/v mixture of methylene chloride and ethanol and there is then added to this solution ethanol, carbon tetrachloride, solvent upper phase of the system $CCl_4:CH_2Cl_2:C_2H_5OH:H_2O$ (2:1:2:1 v/v) and water in that order in amounts sufficient to provide a final solvent system of equal phases as defined above. The phases from the solution are separated and filtered for use in the countercurrent distribution procedure.

In carrying out the countercurrent separation using the preferred apparatus described above, all of the solvent columns except the first are filled with upper phase of the solvent system $CCl_4:CH_2Cl_2:C_2H_5OH:H_2O$ (2:1:2:1 v/v). The first solvent column is then filled with the upper phase of the sample solution as prepared above. Next, lower phase of the sample solution is pumped into the top of the first column on through the other columns top to bottom and out the bottom of the last column. The pumping rate is not critical, but a convenient rate has been found to be about 100 ml. per 24 minutes. Effluent from the last column is collected with a fraction collector for thin layer chromatographic analysis. After all the sample solution lower phase has been used, lower phase of the solvent system $CCl_4:CH_2Cl_2:C_2H_5OH:H_2O$ (2:1:2:1 v/v) is pumped over the columns until monitoring of the effluent fractions and column solutions by thin layer chromatography indicates that separation of the antibiotic components has been effectively completed.

A suitable thin layer chromatographic system for analyzing the various effluent fractions and the solutions in the solvent columns consists of silica gel plates developed with a chloroform:methanol:formic acid (85:15:1 v/v) solvent system. $R_f$ values of the antibiotic components may be determined on such plates by viewing visually and under 2537 Å ultraviolet light. Fractions are combined based on the color bands seen with the above assay and the combined fractions are then concentrated in vacuo at temperatures not exceeding 30°–35° C. The solids from the carminomycin 1-rich fractions are then used in the final chromatographic steps (6) through (8).

After dissolving the partially purified carminomycin 1 obtained in the countercurrent separation procedure in chloroform:methanol (17:3 v/v), this solution is subjected to column chromatography over silica gel using 17:3 (v/v) chloroform:methanol as the eluting solvent. The silica gel used in the column is acid washed to remove iron, dried (≦2% water content), slurried in eluting solvent and adjusted to a pH of between about 7–9 by basification of the slurry, e.g. with concentrated ammonium hydroxide. Eluant fractions from the column are collected and analyzed by the above-described TLC system to determine the fraction(s) which are purified carminomycin 1. The solvent fraction(s) containing the desired purified product may then be treated by conventional means such as concentration or lyophilization to give carminomycin 1 which is sufficiently pure for pharmaceutical use.

The following examples serve to illustrate the invention without limiting it. "Skellysolve B" is the trade name for a petroleum ether fraction of b.p. 60°–68° C. consisting essentially of n-hexane and sold by Skelly Oil Co. All temperatures referred to herein are in degrees Celsius. The abbreviation "MIBK" refers to methyl isobutyl ketone.

Preparation of Starting Materials

A. Crude Carminomycin 1 from Streptosporangium sp. ATCC 31129

Crude carminomycin 1 in the form of an antibiotic mixture or complex (figaroic acid complex) may be obtained by the procedures described in Belgian Patent No. 843,517 or West German Published Application No. 2,628,487. Examples of preferred procedures for the fermentation and recovery of crude carminomycin 1 solids from the culture medium are as follows:

A-1: Shake-flask fermentation

The organism Streptosporangium sp. strain C-31,751 is grown on an agar slant medium consisting of 2 g. D-glucose, 20 g. oatmeal, 2 g. soy peptone and 20 g. agar made up to one liter with distilled water. After at least 6 days growth at 27° C., spores are transferred to a 500 ml. Erlenmeyer flask containing 100 ml. of sterile medium consisting of 50 g. corn starch, 10 g. soy flour, 10 g. peanut meal and 3 g. $CaCO_3$ made up to one liter with distilled water. This vegetative culture is incubated at 27° C. on a rotary shaker (Gyrotory tier shaker, Model G53, New Brunswick Scientific Co., Inc.) set at 210 rev./min. describing a circle with a 5.1 cm. diameter. After 48 hours 4 ml. of culture are transferred to a 500 ml. Erlenmeyer flask containing 100 ml. of sterile production medium consisting of 50 g. sucrose, 20 g. soy flour, 20 g. peanut meal and 3 g. $CaCO_3$ made up to one liter with distilled water. The culture is incubated at 27° C. on a shaker set at 230 rev./min. for 170 hours. At this time antibiotic activity consisting of the figaroic acid complex is found in the culture filtrate and mycelium.

A-2: Tank fermentation

A tank fermentor with 3030 liters of production medium (as in A-1 above) is inoculated with 152 liters of vegetative culture (as prepared in A-1), agitated with an impeller speed of 155 rev./min., aerated at a rate of 1420 liters/min. and incubated at 27° C. The figaroic acid complex is isolated after 210 hours.

A-3: Acid extraction of whole broth with methyl isobutyl ketone (preferred recovery procedure)

Whole broth (21,344 liters) from fermentation of Streptosporangium sp. ATCC 31129 was adjusted from the harvest pH of 8.3 to 3.0-3.4 with 35% $H_2SO_4$ and extracted with 2 volumes of methyl isobutyl ketone. Mat was removed from the thick mixture on a rotary vacuum filter precoated with a diatomaceous earth filter aid. After allowing the phases in the filtrate to separate by gravity, the upper phase (68,828 liters) was separated and concentrated to 413 liters in vacuo using a 20 ft$^2$ Kontro (trademark) evaporator with recycling. Solids were removed on a 3.2 ft$^3$ Niagara (trademark) filter using filter aid and, after rinsing with solvent, the polished liquor was concentrated further to 255 liters. The gummy solids obtained weighed 80.9 kg. and contained 34% filter aid. These were slurried and filtered successively with 324 liter and 160 liter portions of toluene to give 27.4 kg. of active solids. Assay of a sample of the mother liquor showed it to be inactive. The concentrate (255 liters) was diluted with 7.5 volumes of Skellysolve B (trademark) and the precipitate collected on a 1.6 ft$^3$ Niagara filter and washed with another 100 liters of Skellysolve B. The solids were dried at 25°-30° C. to give 2.35 kg. dry amorphous material (active). The active solids (crude figaroic acid complex-impure carminomycin 1) from the above steps were combined for use in Example 1.

B. Crude Carminomycin 1 from Actinomadura carminata

Crude carminomycin 1 may be obtained in the form of an antibiotic complex by following the procedures described in U.K. Pat. No. 1,426,637. An example of a suitable method for obtaining crude carminomycin 1 fermentation solids is as follows:

The culture liquid (700 liters) obtained from growing Actinomadura carminata sp nov. strain No. 4281 (see, for example, Examples 1-3 of U.K. Pat. No. 1,426,637) is acidified with 18% solution of hydrochloric acid to pH 4.5 and allowed to stand for one hour at 50° C. while stirring. The culture liquid is filtered through a fram-type filter press (filter material, belting and calico). The mycelium is dumped to waste. From 600 liters of the solution thus obtained, the antibiotic is extracted with 600 liters of methylene chloride at pH 7.2. The methanol extract may then be concentrated and the impure carminomycin 1 solids precipitated from the concentrated extract by addition of an antisolvent such as diethyl ether, petroleum ether, n-hexane or isomeric hexanes (Skellysolve B).

EXAMPLE 1

A. Sequential Extraction

A suspension of 2.5 kg. of figaroic acid complex (crude carminomycin 1 active solids from Preparation A-3) in 8 liters of $CH_2Cl_2$ was stirred vigorously (1-2 hours) following which the slurry was filtered. The filter cake was washed with 2-4 liters of $CH_2Cl_2$. Following this the filter cake was resuspended in $CH_2Cl_2$(8 liters) and the procedure was repeated. In this manner the solids were extracted a total of four times.

The filter cake from the preceding step was slurried with 8 liters of water, filtered, and the filter cake washed with 3 liters of water. This procedure was carried out a total of four times and the filtrate was discarded.

The filter cake from the preceding step was slurried with 8 liters of methanol and filtered as in the preceding steps. The filter cake was then washed with 8 liters of methanol. This procedure was repeated and the filter cake washed with 4 liters of methanol. The extracts were reduced in volume at reduced pressure and 2-propanol was added to azeotrope any residual water. Diethyl ether was added and the precipitate thus formed was filtered to give 136.2 g. of red solid. The mother liquors were evaporated and the solid precipitated with Skellysolve B and filtered to yield an additional 5.0 g. of red solid. The filter cake was extracted with an additional 8 liters of methanol to give 4.86 g. of red solid. A total of 146.06 g. of solid red material was extracted using methanol.

B. Countercurrent Distribution

A solvent mixture was prepared by mixing 15 liters of carbon tetrachloride, 7.5 liters of methylene chloride, 15 liters of 100% ethyl alcohol and 7.5 liters of deionized water. The two phases of the solvent mixture were allowed to separate and were then bottled.

Five Glenco (Glenco Scientific Inc., Houston, Texas) glass solvent columns (150 cm. ×5 cm.) were filled with Raschig rings (7 mm. ×7 mm.). The columns were connected (bottom of one column to top of next) by Teflon tubing. Columns 2 through 5 were filled with the upper phase of the above-described solvent mixture.

Fifty grams of the red solid from Part A were dissolved in 550 ml. methylene chloride and 550 ml. of 100% ethyl alcohol (with sonification). The solution was put into a 6 liter separatory funnel. There were then added 550 ml. of 100% ethyl alcohol, 1100 ml. carbon tetrachloride, 1100 ml. of solvent upper phase from the above-described $CCl_4:CH_2Cl_2:C_2H_5OH:H_2O$ solvent mixture and 550 ml. of deionized water. The separated phases were then filtered and the first solvent column filled with upper phase.

The lower phase of the sample solvent system was pumped into the top of the first column, out the bottom of the first column, on through the remaining columns and out the bottom of the last column. The pumping rate was about 100 ml. per 24 minutes. One hundred milliliter fractions were taken with a fraction collector from the effluent of the last column. After all the sample solution lower phase was used, lower phase from the $CCl_4:CH_2Cl_2:C_2H_5OH:H_2O$ solvent mixture was pumped over the columns until 120 samples had been taken. The pumping was then stopped and each column was drained and rinsed twice with 100% ethyl alcohol.

Thin layer chromatography was run on each of the fractions and on samples from each of the columns. Ten μl. (some later fractions 20 or 30 μl.) samples of each fraction were put on Quanta-Gram (Quantum Industries, Fairfield, New Jersey) LQDF 20×20 cm. 19 channel silica gel plates. The plates were developed to the top in a system of $CHCl_3:CH_3OH:HCOOH$ (85:15:1) (v/v). After allowing the plates to dry, they were viewed visually and under 2537 Å ultraviolet light.

Fractions were combined based on the color and absorption bands. Fraction I=tubes 3–11, Fraction II=tubes 12–28, Fraction III=tubes 29–54, Fraction IV=tubes 55–71, Fraction V=tubes 72–120, Fraction VI=column 1, Fraction VII=column 2, Fraction VIII=column 3, Fraction IX=column 4 and Fraction X=column 5.

The ten fractions were concentrated under reduced pressure to dryness at a temperature ≦30°–35° C. The samples were scraped from the flasks and were weighed. TLC was run on the products. The results obtained are summarized below.

| Countercurrent Distribution Results | | | | | | |
|---|---|---|---|---|---|---|
| Fraction | Tube No. | Weight | $R_f$ values* of colored components | | | |
| I | 3–11 | 1.85 | 0.3 | 0.65 | 0.7–0.75 | |
| II | 12–28 | 8.01 | 0.3 | 0.37 | 0.55 | 0.65 |
| III | 29–54 | 7.01 | 0.3 | 0.37 | 0.40 | 0.55 |
| IV | 55–71 | 2.23 | 0.3 | 0.33 | 0.37 | 0.40 |
| V | 72–120 | 4.71 | 0.3 | 0.33 | 0.37 | 0.40 |
| VI | Col. 1 | 6.30 | 0.11 | 0.15 | | |
| VII** | Col. 2 | 4.59 | 0.11 | 0.15 | 0.20 | 0.25 | 0.27 |
| VIII | Col. 3 | 4.87 | 0.15 | 0.20 | 0.25 | 0.27 | 0.35 |
| IX | Col. 4 | 4.26 | 0.15 | 0.25 | 0.27 | 0.35 | |
| X | Col. 5 | 3.24 | 0.15 | 0.25 | 0.27 | 0.35 | |
| | | 47.07 g. | | | | |

*TLC determined using LQDF Quanta 19 channel silica gel plates developed with a chloroform-methanol-formic acid system (85:15:1).
**This fraction consisted primarily of carminomycin 1 ($R_f$ = 0.15) plus a number of other compounds in lesser amounts.

C. Adsorption Chromatography

The partially purified carminomycin 1 (Fraction VII from Part B) may then be subjected to adsorption chromatography over silica gel to obtain highly purified (i.e. ≦1% impurity) carminomycin 1. This procedure is carried out as follows:

Silica gel (Grade 62, 85% retained on 200 mesh from W. R. Grace & Co.) is acid washed to remove iron and dried to 2% water content as measured by Karl-Fisher analysis. To a slurry of 1 kg. of the gel in 3 liters of $CHCl_3:CH_3OH$ (17:3 v/v) is added 12 ml. of concentrated $NH_4OH$. The pH of the gel is about 7.5. A 5 cm. ×150 cm. column is slurry packed using the above-prepared silica gel to give a bed height of 130 cm. To the top of the column is added a solution of 5 g. of impure carminomycin 1 in 100 ml. of $CHCl_3:CH_3OH$ (17:3 v/v). The column is developed using $CHCl_3:CH_3OH$ (17:3 v/v) at a flow rate of ∼3.5 ml./min. A forerun of 2000 ml. is collected prior to using a fraction collector. Fractions are then collected and analyzed by the TLC system employed in Part B above. The fraction or fractions containing the purest carminomycin 1 are concentrated to dryness to give highly purified carminomycin 1.

EXAMPLE 2

If in the procedure of Example 1 the crude carminomycin 1 (figaroic acid complex) obtained by fermentation of Streptosporangium sp. ATCC 31129 is replaced by an equal weight of crude carminomycin 1 obtained from *Actinomadura carminata* sp nov. (deposited in the collection of the Institute for the Study of Novel Antibiotics of the Academy of Sciences of the USSR under No. 1NA 4281) as described, for example, in Preparation B above, there is obtained highly purified carminomycin 1.

EXAMPLE 3

A sample of impure (90.4% pure) carminomycin 1 free base derived from fermentation of *Actinomadura carminata* was subjected to the silica gel adsorption chromatography procedure of Example 1, Part C. A 5 g. sample of the carminomycin 1 was dissolved in 100 ml. $CHCl_3:CH_3OH$ (17:3 v/v) and chromatographed on 1 kg. $SiO_2$. Fractions were collected every four minutes. Fractions were analyzed by the TLC system of Example 1, Part B, and like fractions combined to give Fractions 1–8 shown in the following table. These eight fractions were then subjected to Bs-8, ILB and L-1210 bioassays. After concentrating the fractions to dryness, Fraction 6 (2.6682 g.) was found to be the purest carminomycin 1 (<1% impurity).

Silica Gel Chromatography of Impure Carminomycin 1

| Fraction No. | Rf * | BS-8** 4x | 16x | 64x | 256x | 1024x | ILB | L-1210 | Wt. | Impurity Level |
|---|---|---|---|---|---|---|---|---|---|---|
| 1 | 0.78, 0.73, 0.69 | 21 | 18.5 | 16 | 12.5 | RTS | <0.2 | 320M | 0.220 g. | — |
| 2 | 0.20, 0.17 | 23.8 | 20.5 | 17 | 13.5 | 10.3 | 0.05 | 640M | 0.052 | — |
| 3 | 0.17, 0.16 | 24.8 | 22.5 | 18.5 | 13.5 | RTS | 0.8 | 320M | 0.121 | — |
| 4 | 0.17, 0.16 | 25.5 | 23 | 18.8 | 14.2 | RTS | 0.8 | 160M | 0.147 | 2-3% |
| 5 | 0.17, 0.16 | 22.8 | 20.3 | 17.3 | 12.2 | RTS | 0.8 | 320M | 0.6615 | 1-2% |
| 6 | 0.16 | 25.3 | 22.3 | 19.3 | 14 | 11.2 | 0.8 | 160M | 2.6682 | <1% |
| 7 | 0.16 | 25.3 | 22.5 | 18.3 | 14.5 | 11.7 | 0.8 | — | 0.040 | 1-2% |
| 8 | 0.16, 0.10 | 23.8 | 21 | 17.5 | 14 | 11.5 | <0.2 | 320M | 0.295 | >10% |

*TLC system 85:15:1 chloroform:methanol:formic acid on "Quanta" silica gel plates.
**Bacillus subtilis at pH 8 + 4 fold serial dilution - disc plate test TLC of the fractions indicated the presence of at least six impurities (Rf's 0.78, 0.73, 0.69, 0.20, 0.17 and 0.10). The bioassays showed that none of these were more toxic than carminomycin 1 although fractions 2 and 8 showed increased ILB activity. The identity of the impurities is unknown at this time.

We claim:

1. A process for providing the antibiotic carminomycin 1 in purified form from crude fermentation solids containing said antibiotic which comprises the consecutive steps of
   (1) slurrying crude fermentation solids containing carminomycin 1 with methylene chloride and filtering said slurry to recover the filter cake;
   (2) washing the filter cake with water;
   (3) extracting the filter cake from step (2) with methanol and recovering a solid from the concentrated filtered extract by concentration to dryness or precipitation with an antisolvent;
   (4) dissolving the solid from step (3) in equal volumes of the upper and lower phases of the solvent system consisting of methylene chloride, ethanol, carbon tetrachloride and water (2:1:2:1 v/v); said dissolution being accomplished by first dissolving the solid in a 1:1 (v/v) mixture of methylene chloride and ethanol and then adding to this solution ethanol, carbon tetrachloride, solvent upper phase of the system $CCl_4:CH_2Cl_2:C_2H_5OH:H_2O$ (2:1:2:1) (v/v) and water in that order in an amount sufficient to provide a final solvent system as defined above;
   (5) subjecting said solution of step (4) to a countercurrent distribution procedure, said procedure comprising the consecutive steps of:
   (a) providing a countercurrent distribution apparatus having a plurality of packed solvent columns connected in series, said columns being packed with conventional glass or ceramic column packing material;
   (b) filling all except the first column with the upper phase of the solvent system $CCl_4:CH_2Cl_2:C_2H_5OH:H_2O$ (2:1:2:1) (v/v);
   (c) filling the first column with the upper phase of the solution from step (4);
   (d) dispersing the lower phase of the solution from step (4) through the columns while collecting samples of the effluent from the last column until all of the solvent has been employed;
   (e) dispersing the lower phase of the solvent system $CCl_4:CH_2Cl_2:C_2H_5OH:H_2O$ (2:1:2:1) (v/v) through the columns while collecting samples of the effluent from the last column until thin layer chromatographic analysis of the various samples and solutions in the columns indicates cessation of any significant separation of components;
   (f) analyzing the samples taken and the solutions from the columns by thin layer chromatography to detect the carminomycin 1-rich solvent fractions;
   (g) combining the carminomycin 1-rich solvent fractions and recovering the impure carminomycin 1 solids from said combined fractions;
   (6) dissolving the solids from step (5) in chloroform:methanol (17:3) (v/v);
   (7) adsorbing the solution from step (6) on silica gel which has been slurried with chloroform:methanol (17:3) (v/v) and adjusted to a pH of about 7-9; and
   (8) eluting the components of the impure carminomycin 1 mixture with a solvent system consisting of chloroform:methanol (17:3) (v/v) to produce purified carminomycin 1.

2. The process according to claim 1 wherein the crude fermentation solids employed in step (1) are coated onto diatomaceous earth.

* * * * *